US00PP34855P2

(12) United States Plant Patent
Thiede

(10) Patent No.: US PP34,855 P2
(45) Date of Patent: Dec. 20, 2022

(54) ***DIANTHUS* PLANT NAMED 'KLEDG20339'**

(50) Latin Name: ***Dianthus caryophyllus* L.**
Varietal Denomination: KLEDG20339

(71) Applicant: Klemm+Sohn GmbH & Co. KG, Stuttgart (DE)

(72) Inventor: Lena Thiede, Riederich (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/744,609

(22) Filed: May 13, 2022

(30) Foreign Application Priority Data

Jun. 10, 2021 (QZ) ..... PBR 20211321

(51) Int. Cl.
*A01H 5/02* (2018.01)
*A01H 6/30* (2018.01)

(52) U.S. Cl.
USPC ..... Plt./276
CPC ..... *A01H 6/305* (2018.05)

(58) Field of Classification Search
USPC ..... Plt./276, 273
CPC ..... A01H 5/02
See application file for complete search history.

(56) References Cited

PUBLICATIONS

CPVO Register Consultation 4.1.68 Citation for 'KLEDG20339'; Jun. 14, 2022; 1 page.*

* cited by examiner

*Primary Examiner* — Kent L Bell
(74) *Attorney, Agent, or Firm* — Weatherly IP Solutions, LLC; Barbara Campbell

(57) ABSTRACT

A new *Dianthus* plant designated 'KLEDG20339' particularly distinguished by light-pink with dark pink macules, double flowers and an upright habit, is disclosed.

1 Drawing Sheet

Genus and species: *Dianthus caryophyllus* L.
Variety denomination: 'KLEDG20339'.

CROSS-REFERENCE TO RELATED APPLICATIONS

This application claims priority to and the benefit of Community Plant Variety Rights Application File No. 2021/1321, filed on Jun. 10, 2021, the entire contents of which are incorporated herein by reference for all purposes.

BACKGROUND OF THE NEW PLANT

The present invention comprises a new and distinct variety of *Dianthus*, botanically known as *Dianthus caryophyllus* L., and hereinafter referred to by the variety name 'KLEDG20339'. 'KLEDG20339' originated from a controlled cross in May 2015 in Stuttgart, Germany between the proprietary female *Dianthus* parent 'DSS-2014-1001' (unpatented) and the proprietary male *Dianthus* parent 'DSS-2014-1007' (unpatented). 'KLEDG20339' was selected in July 2016 from a population of plants grown resulting from the initial cross.

In August 2016, 'KLEDG20339' was first vegetatively propagated by vegetative stem cuttings in Stuttgart, Germany and Latina, Italy. 'KLEDG20339' was found to reproduce true to type in successive generations of asexual propagation in Latina, Italy and Stuttgart, Germany via vegetative cuttings.

SUMMARY

The following are the most outstanding and distinguishing characteristics of 'KLEDG20339' when grown under normal horticultural practices in Stuttgart, Germany.

1. Light pink with dark pink macules, double flowers; and
2. An upright habit.

DESCRIPTION OF THE PHOTOGRAPH

This new *Dianthus* plant is illustrated by the accompanying photograph of an 11-week-old plant taken in April 2018 and grown in a greenhouse in Stuttgart, Germany. The colors shown are as true as can be reasonably obtained by conventional photographic procedures. The photograph is a whole plant photo of 'KLEDG20339' and shows the foliage, buds, and flowers.

DESCRIPTION

The following detailed descriptions set forth the distinctive characteristics of 'KLEDG20339'. The data which define these characteristics were collected from asexual reproductions carried out in Stuttgart, Germany. Data was collected in March 2022 from plants that were 6-months-old and grown in a plastic greenhouse. Color references are to The R.H.S. Colour Chart of The Royal Horticultural Society of London (R.H.S.), 5$^{th}$ edition (2007).

Classification:
*Family*.—Caryophyllaceae.
*Botanical*.—*Dianthus caryophyllus* L.
*Designation*.—'KLEDG20339'.
*Type*.—Pot carnation.

Parentage:
*Female parent*.—'DSS-2014-1001' (unpatented).
*Male parent*.—'DSS-2014-1007' (unpatented).

Plant:

*Propagation type.*—Vegetative stem cuttings, terminal cuttings.

*Time to produce a rooted young plant.*—10 to 14 days.

*Root description.*—Fine; young roots are RHS 161D (Greyed-Yellow) and mature roots are RHS 199C (Grey-Brown).

*Rooting habit shape.*—Lanceolate.

*Plant form.*—Upright.

*Plant height.*—11.0 cm to 13.0 cm.

*Plant diameter or spread.*—16.0 cm to 18.0 cm.

*Hardiness.*—Winter-hardy under conditions in Germany.

Lateral branches/stems:

*Shape of the branch in cross-section.*—Circular.

*Hollowness of the branch.*—Absent.

*Length.*—6.0 cm to 9.0 cm.

*Diameter.*—3.0 cm to 4.0 cm.

*Internode length.*—2.0 cm to 2.5 cm.

*Internode quantity per branch.*—3 to 4.

*Node length.*—0.2 cm to 0.4 cm.

*Node diameter.*—0.2 cm to 0.4 cm.

*Texture.*—Smooth.

*Color.*—RHS 146C (Yellow-Green).

*Flower clustering on the lateral branch.*—None.

Foliage:

*Arrangement.*—Opposite.

*Length.*—4.0 cm to 5.0 cm.

*Width.*—0.3 cm to 0.5 cm.

*Shape.*—Lanceolate.

*Apex.*—Acute.

*Base.*—Obtuse.

*Margin.*—Entire.

*Texture (both upper and lower surfaces).*—Smooth.

*Cross-section of the leaf.*—Moderately concave.

*Curvature of the leaf.*—Absent.

*Glaucosity of the leaf.*—Weak.

*Leaf color (both immature and mature).*—Upper surface: RHS 137C (Green) for immature and RHS 138A (Green) for mature. Lower surface: RHS 137C (Green) for immature and RHS 138A (Green) for mature.

*Venation pattern.*—Absent.

Flowers:

*Flower type.*—Double; 3 to 5 flowers per spray.

*Fragrance.*—Present.

*Position of the flowers compared to the foliage of the plant.*—Same level.

*Profile of both the upper and lower part in the lateral view.*—Upper is flat-convex and lower is flat-convex.

*Diameter of flower.*—3.0 cm to 3.5 cm.

*Natural flowering season.*—Spring to Autumn.

*Flower longevity on the plant.*—14 to 19 days.

Buds:

*Length.*—0.8 cm to 1.5 cm.

*Diameter.*—0.4 cm to 0.6 cm.

*Shape.*—Elliptic.

*Color.*—RHS 138A (Green).

*Extrusion of the styles at the bud stage.*—Absent.

Corolla:

*Quantity of petals and arrangement.*—13 to 15 and arranged in several whorls.

*Corolla height.*—1.0 cm to 1.5 cm.

*Petal length.*—2.5 cm to 3.0 cm.

*Petal width.*—0.8 cm to 1.3.

*Petal shape.*—Spoon-shaped.

*Petal apex.*—Obtuse.

*Petal base.*—Acute.

*Petal margin.*—Serrated.

*Depth of petal margin.*—Medium.

*Petal texture (both upper and lower surfaces).*—Smooth.

*Petal color.*—Immature: Upper surface: RHS 49A. Lower surface: RHS 49B. Mature: Upper surface: RHS 50D with RHS 50B macules being present under high light conditions; 1 macule per petal. Lower surface: RHS 50D.

*Calyx.*—Quantity of sepals: Composed of 5 sepals. Longitudinal axis of the lobes of the calyx: Concave. Shape: Campanulate. Calyx height: 0.8 cm to 1.5 cm. Calyx diameter (at the apex): 0.4 cm to 0.6 cm. Sepal texture (both upper and lower surfaces): Smooth. Sepal color: Upper surface: RHS 137A (Green). Lower surface: RHS 137D (Green).

*Position of the outer lobes of the epicalyx in relation to the calyx.*—Free.

*Apex shape of the outer lobes of the epicalyx.*—Medium acuminate.

*Tip length of the outer lobes of the epicalyx.*—0.2 cm to 0.3 cm.

*Apex shape of the inner lobes of the epicalyx.*—Short acuminate.

*Tip length of the inner lobes of the epicalyx.*—0.3 cm to 0.5 cm.

Peduncles:

*Length.*—5.0 cm to 8.0 cm.

*Diameter.*—0.2 cm.

*Strength.*—Moderate.

*Texture.*—Smooth.

*Color.*—RHS 146C (Yellow-Green).

Reproductive organs:

*Stamens.*—Quantity per flower: Low (less than two). Filament length: 0.5 cm to 0.6 cm. Filament color: RHS 8D (Yellow). Anther length: 0.1 cm. Anther diameter: 0.05 cm. Anther color: RHS 18C (Yellow-Orange). Pollen amount: Sparse. Pollen color: RHS 158A (Yellow-White).

*Pistils.*—Quantity per flower: 2. Length: 0.5 cm to 0.8 cm. Diameter: 0.05 cm. Stigma: Color: RHS 155D (White). Shape: Straight. Length: 0.3 cm. Diameter: 0.05 cm. Style: Color: RHS 155D (White). Length: 0.5 cm. Diameter: 0.05 cm. Ovary: Color: RHS 145A (Yellow-Green). Width: 0.3 cm to 0.4 cm. Length: 0.5 cm to 0.7 cm. Shape: Obovate.

Fruit and seed set: Observed but no information is available.

Disease and pest/insect resistance: No disease and pest/insect resistance observed.

COMPARISON WITH PARENTAL LINES AND KNOWN VARIETY

'KLEDG20339' is distinguished from the parental lines as described in Table 1.

TABLE 1

| Comparison with Parental Lines | | | |
|---|---|---|---|
| Characteristic | 'KLEDG20339' | Female Parent 'DSS-2014-1001' | Male Parent 'DSS-2014-1007' |
| Flower type | Double | Single | Double |
| Flower color, general color description | Light pink with dark pink macules | Pink with purple ring | Salmon with purple ring |

'KLEDG20339' can be compared to the commercial *Dianthus* variety 'KLEDG10117' (U.S. Plant Pat. No. 23,330). Differences between the varieties are described in Table 2.

TABLE 2

| Comparison with Similar Variety | | |
|---|---|---|
| Characteristic | 'KLEDG20339' | 'KLEDG10117' |
| Flower color, upper surface, mature | RHS 50D with RHS 50B macules being present | RHS N74D (Red-Purple) with RHS 64A (Red-Purple) eyes under high light conditions |
| Peduncle length | 5.0 cm to 8.0 cm | 8.0 cm to 10.0 cm |

I claim:

1. A new and distinct variety of *Dianthus* plant designated 'KLEDG20339' as illustrated and described herein.

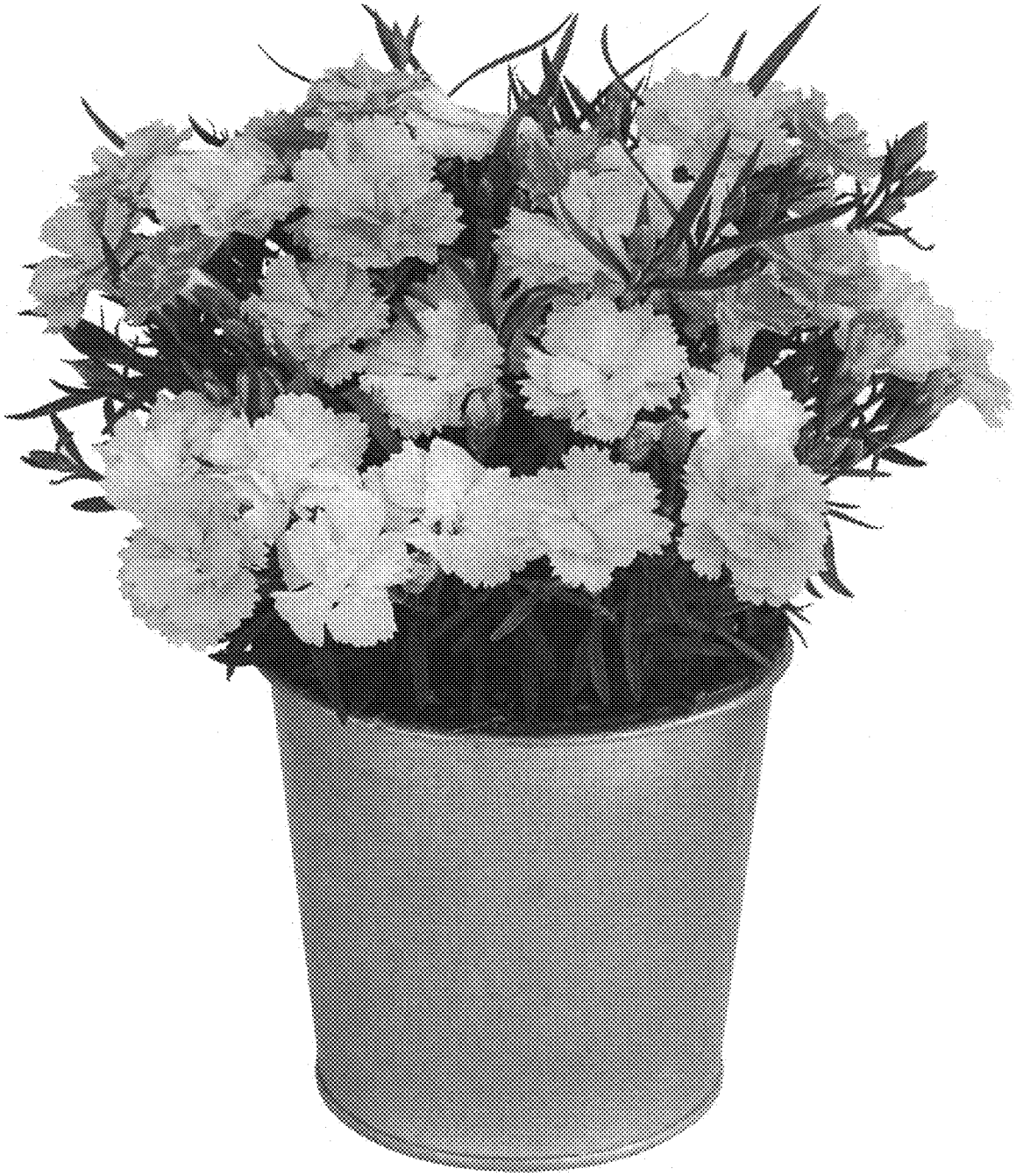

* * * * *